(12) United States Patent
Paul (10) Patent No.: US 9,427,265 B2
(45) Date of Patent: *Aug. 30, 2016

(54) SURGICAL INSTRUMENT SYSTEM AND METHOD (71) Applicant: Warsaw Orthopedic, Inc., Warsaw, IN (US)

(72) Inventor: Marc T. Paul, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 130 days.

This patent is subject to a terminal disclaimer.

(21) Appl. No.: 14/161,923

(22) Filed: Jan. 23, 2014

(65) Prior Publication Data

US 2015/0201975 A1 Jul. 23, 2015

(51) Int. Cl.
*A61B 17/70* (2006.01)
*A61B 17/17* (2006.01)

(52) U.S. Cl.
CPC ....... *A61B 17/7074* (2013.01); *A61B 17/1728* (2013.01); *A61B 17/1757* (2013.01)

(58) Field of Classification Search
CPC .......... A61B 17/7074; A61B 17/7076; A61B 17/7059
USPC ....... 606/280, 281, 289, 295, 99, 104, 86 A, 606/86 B
See application file for complete search history.

(56) References Cited

U.S. PATENT DOCUMENTS

| 5,423,826 A * | 6/1995 | Coates et al. ................... 606/96 |
| 6,746,454 B2 * | 6/2004 | Winterbottom et al. ....... 606/99 |
| 7,166,111 B2 * | 1/2007 | Kolb et al. ...................... 606/96 |
| 7,468,064 B2 * | 12/2008 | Bruneau et al. ................ 606/99 |
| 2004/0204717 A1 * | 10/2004 | Fanger et al. .................. 606/96 |

* cited by examiner

*Primary Examiner* — Pedro Philogene
*Assistant Examiner* — David C Comstock (57) ABSTRACT

A surgical guide comprises a member including an inner surface defining a cavity configured for disposal of at least one surgical instrument. The member further includes at least one locking element configured for mating engagement with a spinal implant such that the member is rotatable relative to the spinal implant to selectively orient the at least one surgical instrument. Systems and methods are disclosed.

20 Claims, 5 Drawing Sheets

SURGICAL INSTRUMENT SYSTEM AND METHOD

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms inducting deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, discectomy, laminectomy, correction and implantable prosthetics. As part of these surgical treatments, implants such as bone fasteners, plates, connectors and vertebral rods are often used to provide stability to a treated region. These implants can redirect stresses away from a damaged or defective region while healing takes place to restore proper alignment and generally support the vertebral members. For example, plates may be attached via the fasteners to the exterior of one or more vertebral members. This disclosure describes an improvement over these prior art technologies.

SUMMARY

In one embodiment, a surgical guide is provided. The surgical guide comprises a member including an inner surface defining a cavity configured for disposal of at least one surgical instrument. The member further includes at least one locking element configured for mating engagement with a spinal implant such that the member is rotatable relative to the spinal implant to selectively orient the at least one surgical instrument. In some embodiments, systems and methods are provided.

BRIEF DESCRIPTION OF THE DRAWINGS

The present disclosure will become more readily apparent from the specific description accompanied by the following drawings, in which.

DETAILED DESCRIPTION

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine.

In some embodiments, the present surgical system includes a guide configured for disposal of a surgical instrument(s) and attachment to a spinal implant(s) such that the guide is manipulable relative to the implant to selectively orient the surgical instrument for treating a spine. In one embodiment, the present surgical system includes a surgical guide, such as, for example, a drill, tap and screw (DTS) guide, which can be employed with a plating system for attachment and/or docking. In one embodiment, the surgical guide allows for holding, drilling, tapping and screwing with limited invasiveness to a subject body. In one embodiment, the surgical guide can be employed with a low profile plating system for various orthopedic applications.

In one embodiment, the surgical guide comprises a drill guide that has a quick attach mechanism to allow for quick attachment and to secure a plate. In one embodiment, the surgical guide allows placement of the plate over a distractor pin. For example, once a plate is positioned in a selected location, the user can drill, tap and/or drive a screw through the guide. In one embodiment, the surgical guide is rotatable and/or pivotable relative to the implant. In one embodiment, the surgical guide allows for cephalad-caudal angular variability of surgical instruments, which is equal to the variability of an allowable screw angle of a plate.

In one embodiment, the surgical guide comprises a lock and/or mating element such as, for example, dimples on a distal end of the surgical guide to engage a lock and/or mating element such as, for example, detents on a first side and a second side of an implant such as, for example, a spinal plate. In some embodiments, the surgical guide is rotatable relative to the implant and allows for the user to change the angle while holding an implant in position. In one embodiment, a pivot point of the surgical guide is disposed in alignment with a head of a screw such that the guide can be variably angled relative to the implant. In one embodiment, while holding a plate in place, the user can adjust the screw angle of the guide to fix the guide such that the guide avoids or prevents interference as the screw angle changes.

In one embodiment, one or all of the components of the surgical system are disposable, peel-pack, pre-packed sterile devices used with an implant. One or all of the components of the surgical system may be reusable. The surgical system may be configured as a kit with multiple sized and configured components. In one embodiment, the surgical system includes one or a plurality of guides that may be employed with one or a plurality of surgical instruments and/or one or a plurality of alternate surgical instruments.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, in some embodiments, as used in the specification and including the appended claims, the singular forms "a", "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-5, there are illustrated components of a surgical system 10, including a surgical instrument, such as, for example, a surgical guide 12 in accordance with the principles of the present disclosure.

The components of system 10 can be fabricated from biologically acceptable materials suitable for medical applications, including metals, synthetic polymers, ceramics and bone material and/or their composites. For example, the components of system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

The components of system 10 including surgical guide 12 are employed, for example, with a minimally invasive procedure, including percutaneous techniques, mini-open and open surgical techniques to deliver and introduce an implant, such as, for example, one or a plurality of bone fasteners and/or spinal plates, at a surgical site within a body of a patient, for example, a section of a spine. In some embodiments, surgical guide 12 delivers and introduces a spinal plate for fixation with an anterior side of a spine. In some embodiments, surgical guide 12 is configured to facilitate drilling and/or tapping of tissue, such as, for example, vertebrae, and/or guiding, fastening and/or driving fasteners, such as, for example, bone screws with the vertebrae using one or a plurality of surgical tools and/or instruments, which instruments may be alternately disposed with surgical guide 12 during a procedure.

Surgical guide 12 is configured for disposal of one or a plurality of surgical instruments and/or alternate surgical instruments, and for movable engagement with and relative to a spinal implant to selectively orient the surgical instrument, as described herein. Surgical guide 12 includes a member, such as, for example, a guide housing 14. In some embodiments, housing 14 is configured to align and/or direct a surgical instrument, as described herein, relative to a spinal implant to selectively orient the surgical instrument for treating a spine. Housing 14 extends between a proximal end 16 and a distal end 18. Housing 14 defines a longitudinal axis x.

Housing 14 includes a handle 22. Handle 22 extends to connect and merge with a portion of housing 14, which includes a uniformly configured shaft 20, via an outer surface 21 of shaft 20. In some embodiments, handle 22 and shaft 20 have a tapered connection. In one embodiment, handle 22 comprises an arcuate configuration. In one embodiment, handle 22 has a flexible configuration, which includes movement in a lateral or side to side direction. In some embodiments, all or only a portion of handle 22 may have a semi-rigid, rigid, flexible or elastic configuration, and/or have elastic and/or flexible properties, such as the elastic and/or flexible properties corresponding to the material examples described herein such that handle 22 provides a selective amount of expansion and/or extension in an axial direction. In some embodiments, the material of handle 22 is, such as, for example, a pliable, flexible, spring-like material and/or a material configured to retain its configuration, such as, for example, Nitinol. In some embodiments, handle 22 may be compressible in an axial direction. In some embodiments, handle 22 comprises an irregular, tapered, offset, variable, staggered and/or non-uniform configuration. Handle 22 includes a surface, such as, for example, a gripping surface 24 configured to facilitate maneuvering of surgical guide 12.

Figure 1:
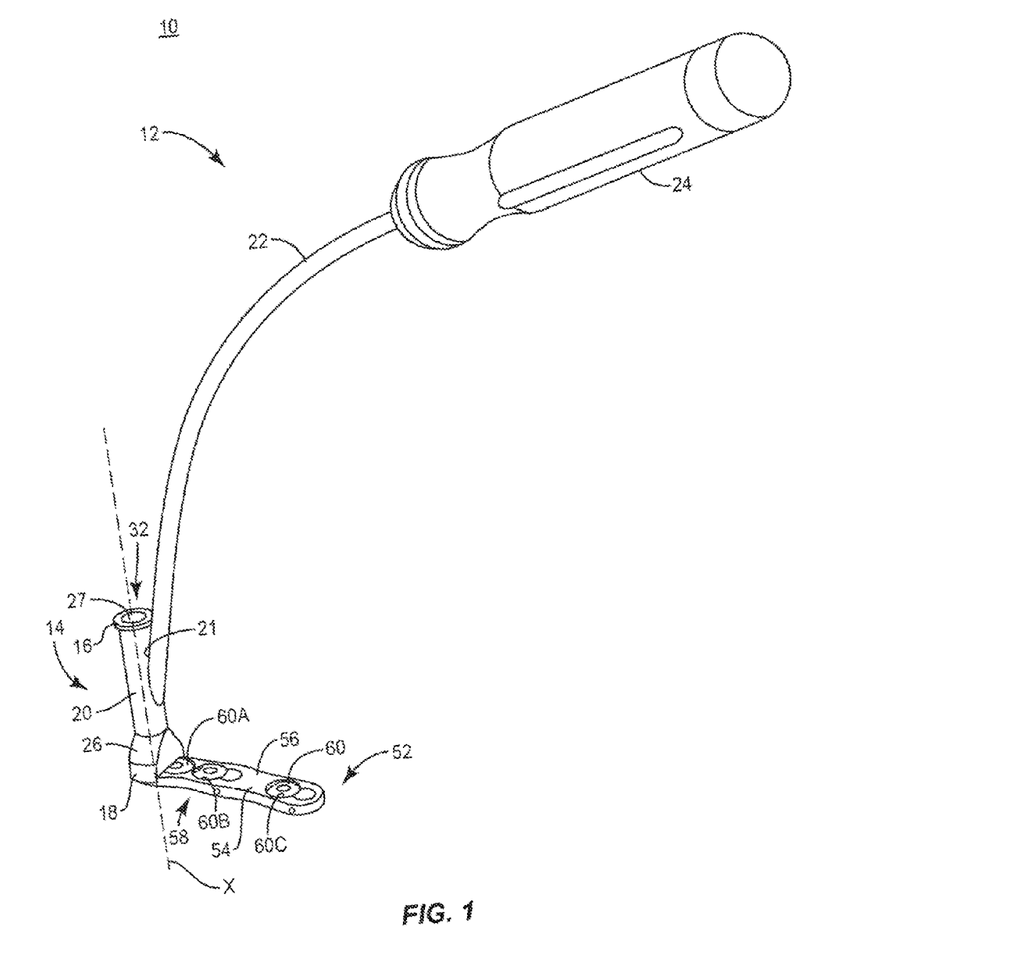
FIG. 1 is a perspective view of components of one embodiment of a surgical system in accordance with the principles of the present disclosure.
Figure 2:
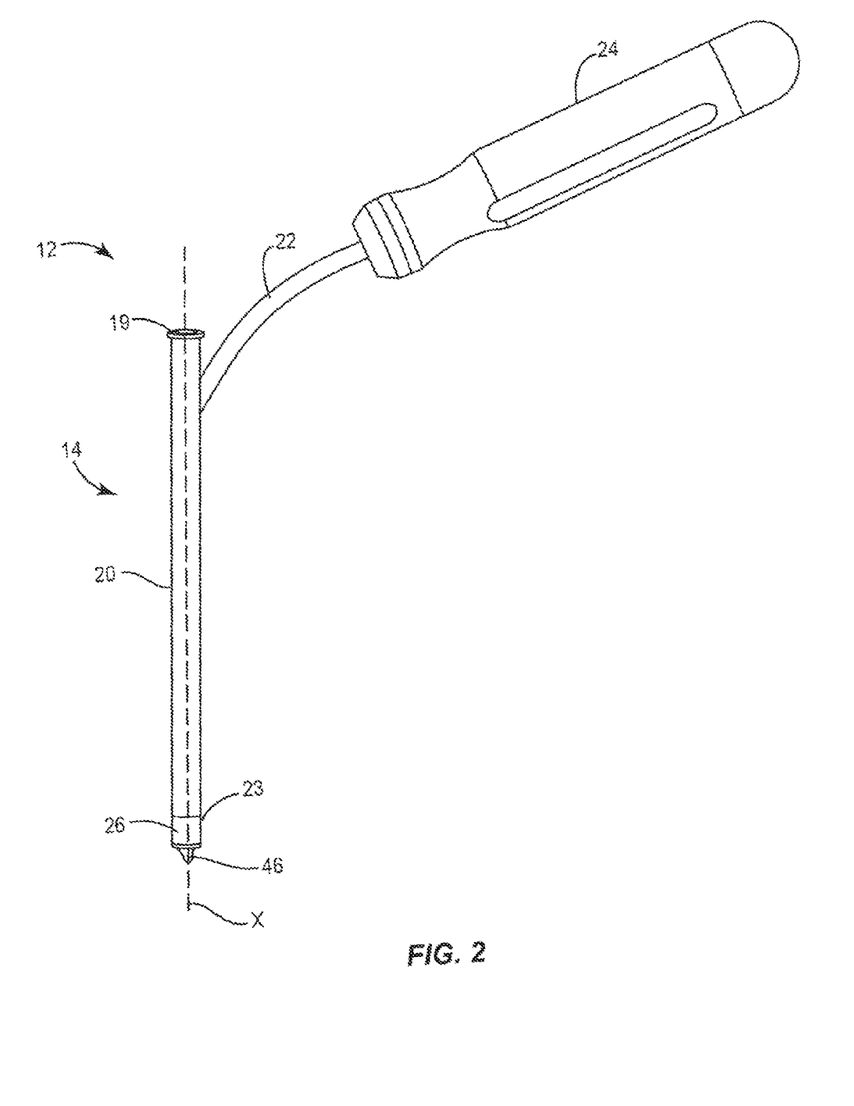
FIG. 2 is a side view of components of one embodiment of a surgical system in accordance with the principles of the present disclosure.

Housing 14 includes shaft 20 and a base 26 extending therefrom. As shown in FIG. 1, shaft 20 and base 26 are monolithically formed. In some embodiments, shaft 20 and base 26 can be separate and attachable or include fastening elements for attachment, integrally connected and/or adhered to via adhesive. As shown in FIG. 2, shaft 20 extends between an end 19 and an end 23. Shaft 20 has a uniform cylindrical cross section configuration and a uniform dimension such as, for example, diameter d1. In some embodiments, shaft 20 may have alternate cross section configurations such as, for example, oval, oblong, triangular, rectangular, square and/or polygonal.

Base 26 includes a portion 25 having a substantially elliptical configuration and a tapered configuration that increases from a dimension, such as, for example, a width t1 to a dimension, such as, for example, a width t2 at end 18. Base 26 includes a capture portion 29 that extends from portion 25 and includes extensions, as described herein. Capture portion 29 has a larger width t2 for capture of a spinal implant, such as, for example, a plate 52, such that plate 52 can securely lock into base 26, as described herein. In some embodiments, base 26 may have various configurations, such as, for example, oval, rectangular, polygonal, irregular, tapered, offset, staggered, uniform and non-uniform.

Shaft 20 includes an opening 27 defined by surface 21 and an inner surface 28. In some embodiments, surface 28 has various surface configurations, such as, for example, rough, threaded for connection with surgical instruments, arcuate, undulating, porous, semi-porous, dimpled, polished and/or textured. Surface 28 defines a wall 30 that defines a cavity 32 which extends through shaft 20 and base 26. Cavity 32 is configured for disposal of at least one surgical instrument. In some embodiments, cavity 32 may have alternate cross-sectional configurations, such as, for example, oval, oblong, triangular, rectangular, square, polygonal, irregular, uniform, non-uniform, variable and/or tapered.

Wall 30 includes at least one extension, such as, for example, an extension 34 and an extension 36. In some embodiments the width of extensions 34, 36 may be uniformly increasing or decreasing, or constant. Wall 30 includes an elongate opening, such as, for example, a slot 33. Slot 33 is configured to facilitate flexion and retraction of extensions 34, 36 such that extensions 34, 36 are configured to flex outwardly to overcome a resilient inward bias of housing 14 to receive, capture and/or release plate 52, as described herein.

Slot 33 extends from capture portion 29 into a portion of shaft 20. Slot 33 terminates at a relief portion, such as, for example, an opening 35. Opening 35 facilitates flexion and retraction of extensions 34, 36 and allows extensions 34, 36 to flex a predetermined amount and retract back into their original position to facilitate engagement and/or release of plate 52. In some embodiments, slot 33 and/or opening 35 are variously configured, such as, for example, oval, oblong, triangular, rectangular, square, polygonal, irregular, uniform, non-uniform, horseshoe shape, U-shape, kidney bean shape, variable and/or tapered.

Extension 34 includes a locking element, such as, for example, a protuberance 38, oriented in a first direction. Extension 36 includes a locking element, such as, for example, a protuberance 42, oriented in a second, opposing direction. Protuberances 38, 42 are configured for mating engagement with plate 52, as described herein. In one embodiment, extensions 34, 36 include a plurality of protuberances spaced apart about surface 28. In one embodiment, extension 34 and/or extension 36 includes a plurality of protuberances spaced apart about surface 28. In some embodiments, protuberances 38, 42 may include tabs, hooks, adhesives, snaps, spring loaded buttons, flanges, pins, clips and/or magnets.

Figure 3:
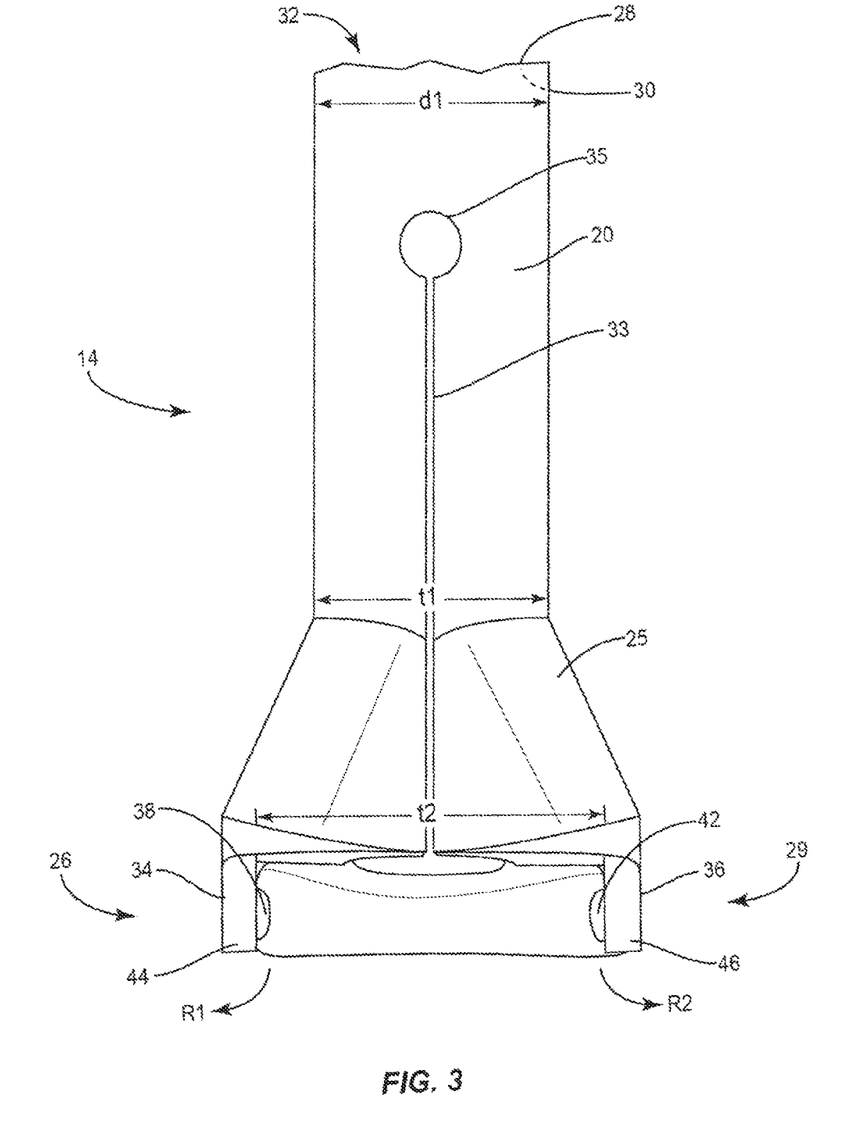
FIG. 3 is an enlarged front view of components of the system shown in FIG. 1.

As shown in FIG. 3, extension 34 comprises a resilient inward biased prong 44 that includes protuberance 38 and extension 36 comprises a resilient inward biased prong 46 that includes protuberance 42. Prong 44 flexibly pivots with extension 34 and prong 46 flexibly pivots with extension 36. Prongs 44, 46 are configured to facilitate flexion and retraction of extensions 34, 36 to receive, capture and/or release plate 52.

System 10 includes plate 52, which includes a stratum 54 having an upper surface 56 and a lower surface 58. Surface 58 is configured to engage tissue, such as, for example, an anterior portion of cervical vertebrae. Stratum 54 defines a series of openings 60 extending between surfaces 56, 58. Openings 60 are configured for disposal of permanent implantable fixation elements, such as, for example, bone screws (not shown) for attaching plate 52 with tissue. In one embodiment, plate 52 includes three openings 60a, 60b and 60c. Stratum 54 defines an edge 62 disposed around the entire periphery P of plate 52.

Edge 62 includes a surface 64 defining detents 66 configured for mating engagement with protuberances 38, 42. In one embodiment, surface 64 defines a plurality of detents 66, such as, for example, detents 66a, 66b and 66c. Detents 66a, 66b and 66c each include pairs of detents disposed on opposite sides of openings 60. In some embodiments, surface 64 may have alternate surface configurations, such as, for example, rough, threaded for connection with surgical instruments, arcuate, undulating, porous, semi-porous, dimpled, polished and/or textured. In some embodiments, plate 52 may have various configurations, such as, for example, oval, oblong, triangular, square, polygonal, irregular, uniform, non-uniform, variable and/or tapered.

Figure 4:
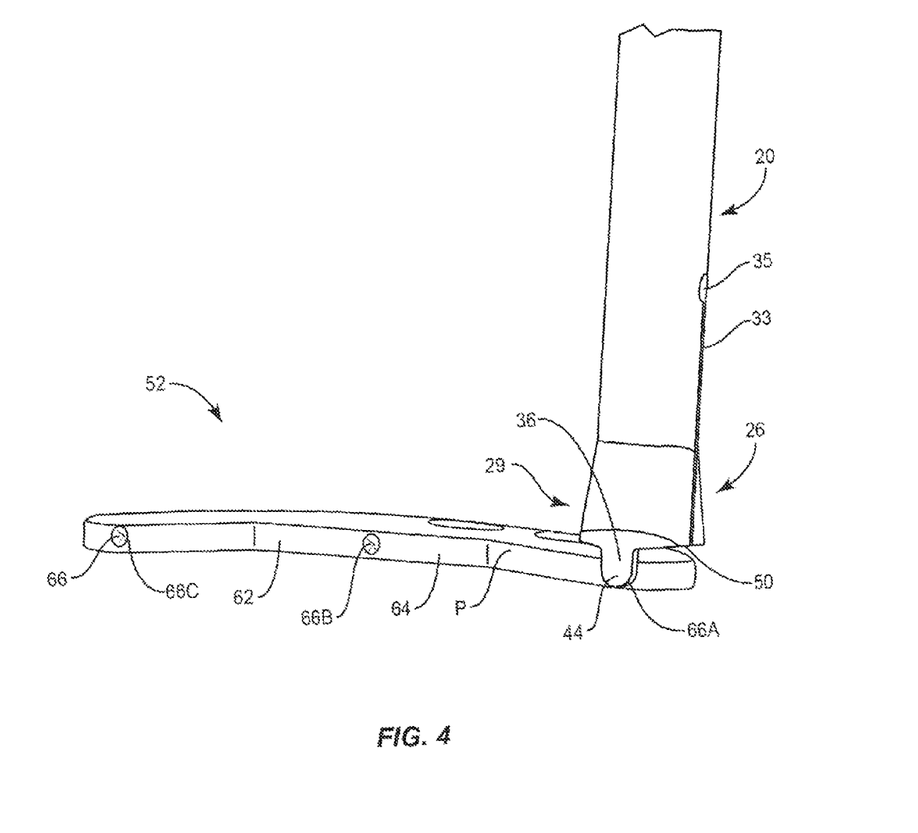
FIG. 4 is a side view of components of the system shown in FIG. 1.

Protuberances 38, 42 are configured to matingly engage detents 66 on opposite sides of edge 62 to releasably secure surgical guide 12 with plate 52 for delivery and/or introduction at a surgical site. In one embodiment, the cross-section configuration of detents 66 may correspond to the cross-section configuration of protuberances 38, 42. For example, as shown in FIGS. 3 and 4, protuberances 38, 42 have hemi-spherical configurations and detents 66 define recesses having mating hemi-spherical configurations. In some embodiments, protuberances 38, 42 and/or detents 66 may have alternate cross-section configurations, such as, for example, round, oval, oblong, triangular, rectangular, square, polygonal, irregular, uniform, non-uniform, variable and/or tapered.

Protuberances 38, 42 engage edge 62 such that prongs 44, 46 flexibly pivot with extensions 34, 36 and are caused to flex outwardly via slot 33, as described herein, to receive, capture and/or release plate 52. During expansion, extensions 34, 36 expand, in the direction shown by arrows R1, R2 in FIG. 3. Protuberances 38, 42 engage the surface of edge 62 that defines detents 66 to matingly engage with surface 64, as shown in FIG. 4.

Prongs 44, 46 flexibly pivot due to the inward bias of extensions 34, 36 such that protuberances 38, 42 matingly engage surface 64 of detents 66 in a pressure or friction fit. As such, extensions 34, 36 capture plate 52 in a releasable engagement and locked position. In the locked position, extensions 34, 36 engage plate 52 with housing 14 to prevent translation of plate 52 and resist disengagement of plate 52 from surgical guide 12. In the locked position, housing 14 is rotatable and/or pivotable relative to plate 52, as described herein, via manipulation of handle 22. In some embodiments, surgical guide 12 is rotatable and/or pivotable relative to plate 52 in non-locking positions. In some embodiments, surgical guide 12 is rotatable and/or pivotable relative to plate 52 about a pivot point disposed in alignment with openings 60.

Figure 5:
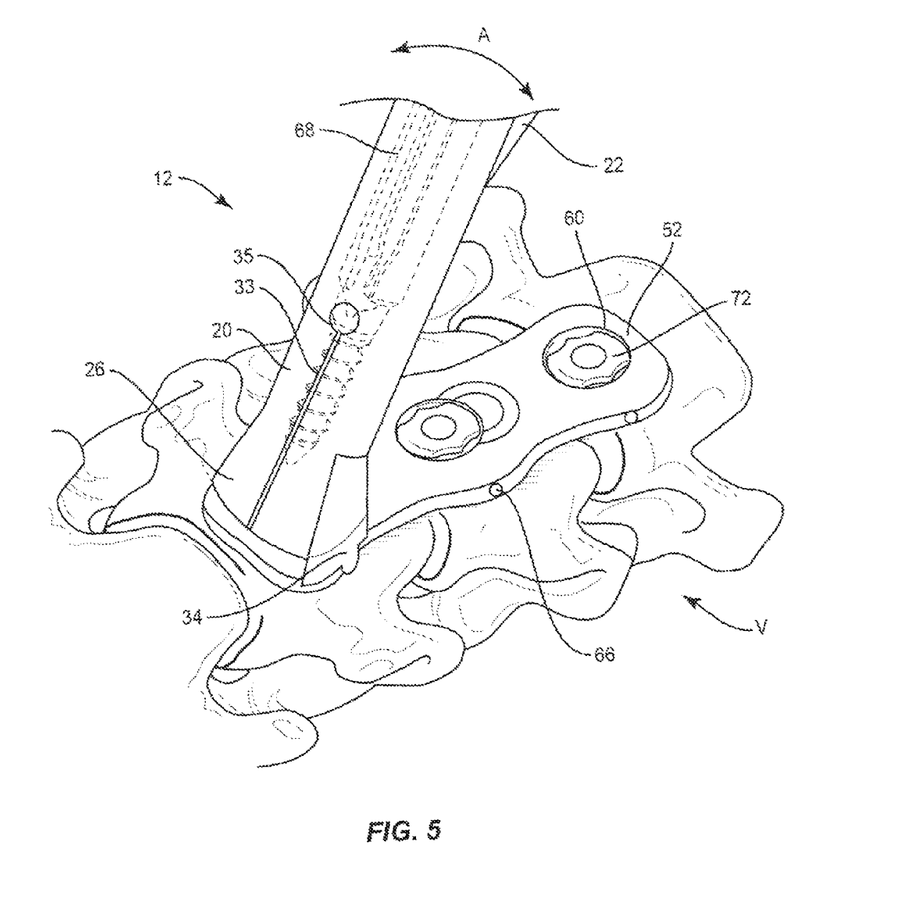
FIG. 5 is a perspective view of components of one embodiment of a surgical system in accordance with the principles of the present disclosure disposed with vertebrae.

System 10 includes a surgical instrument, such as, for example, a bone screw driver 68, as shown in phantom in FIG. 5. Driver 68 is configured for disposal within cavity 32 such that when protuberances 38, 42 matingly engage plate 52 in a lacked position, handle 22 is manipulated such that housing 14 is rotatable relative to plate 52 to selectively orient driver 68 for engagement with plate 52.

In some embodiments, the surgical instrument includes at least one of a plurality of alternate instruments. In some embodiments, the surgical instrument can include a drill, a tap and/or or a driver. In one embodiment, housing 14 pivots about plate 52 to selectively orient instrument 68 relative to vertebral tissue. In one embodiment, housing 14 rotates along a cephalad-caudal plane of a body. In some embodiments, surgical system 10 may include a surgical instrument, which comprises distractor pins that are disposable along cavity 32 and engageable with vertebral tissue to distract vertebrae.

In some embodiments, one or more of the surfaces of housing 14 include a layer of friction-reducing material (not shown). In some embodiments, the layer may include an insert and/or a coating comprising silicone, poly(tetrafluororthene), lubricants and/or material examples, as described herein. In some embodiments, the layer of friction-reducing material provides an even interface between surface 28 and an outer surface of an driver 68.

In assembly, operation and use, surgical system 10, as shown in FIG. 5, similar to the systems and methods described herein, is employed to treat a selected section of cervical vertebrae V. A medical practitioner obtains access to a surgical site including vertebrae V in any appropriate manner, such as through incision and retraction of tissues. In some embodiments, system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating a spine disorder.

An incision is made in the body of a patient and a cutting instrument (not shown) creates a surgical pathway for implantation of components of system 10 with an anterior portion of cervical vertebrae V. A preparation instrument (not shown) can be employed to prepare tissue surfaces of vertebrae V, as well as for aspiration and irrigation of a surgical region.

Surgical guide 12, described herein, comprises a drill, tap, and screw guide. Surgical guide 12 is connected with plate 52, bone screws 72 and/or other components of system 10 for orientation and delivery of the components of system 10 along the surgical pathway. Surgical guide 12 introduces the components of system 10 along the surgical pathway to implant plate 52 and/or bone fasteners 72 with vertebrae V.

Surgical guide 12 is disposed adjacent plate 52 for connection with plate 52. Handle 22 is manipulated to orient housing 14 such that protuberances 38, 42 engage plate 52 and prongs 44, 46 flex outwardly to receive plate 52, as described herein. Extensions 34, 36 expand and protuberances 38, 42 engage the surface of edge 62 that define detents 66 to matingly engage with surface 64. Prongs 44, 46 flexibly pivot due to the inward bias of extensions 34, 36 such that protuberances 38, 42 matingly engage surface 64 of detents 66 in a pressure or friction fit. As such, extensions 34, 36 capture plate 52 in a releasable engagement and locked position. In the locked position, extensions 34, 36 engage plate 52 with housing 14 to prevent translation of plate 52 and resist disengagement of plate 52 from surgical guide 12.

Surgical guide 12 is an adaptable instrument configured to perform multiple applications during a surgical procedure. In the locked position, housing 14 is rotatable and/or pivotable relative to plate 52, in the direction shown by arrows A in FIG. 5, via manipulation of handle 22 about a pivot point disposed in alignment with openings 60. A surgical tap and/or drill is passed through housing 14 and oriented therewith via rotation or pivoting of housing 14 relative to plate 52 and/or vertebral tissue, in the direction shown by arrows A, to prepare and/or create a cavity in tissue of vertebrae V.

Pilot holes or the like are made in selected vertebra of vertebrae V for receiving bone screws 72. Driver 68 is attached with bone screws 72 and passed through housing 14 to adjacent plate 52 via rotation or pivoting of housing 14 relative to plate 52 and/or vertebral tissue, in the direction shown by arrows A. Driver 68 is engaged with bone screws 72 to torque, fasten or otherwise attach bone screws 72 to plate 52 and vertebral tissue to fasten plate 52 with vertebrae V.

Upon completion of the procedure, the surgical instruments, assemblies and non-implanted components of system 10 are removed and the incision is closed. System 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of system 10. In some embodiments, system 10 may include one or a plurality of plates, connectors and/or bone fasteners for use with a single vertebral level or a plurality of vertebral levels.

In some embodiments, system 10 includes one or more fasteners that may be engaged with tissue in various orientations, such as, for example, series, parallel, offset, staggered and/or alternate vertebral levels. In some embodiments, one or more of the fasteners may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In some embodiments, one or all of the components of system 10 can be delivered or implanted as a pre-assembled device or can be assembled in situ. The components of system 10 may be completely or partially revised, removed or replaced.

In one embodiment, system 10 includes an agent, which may be disposed, packed, coated or layered within, on or about the components and/or surfaces of system 10. In some embodiments, the agent may include bone growth promoting material, such as, for example, bone graft to enhance fixation of the components and/or surfaces of system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical guide comprising:
a member including a shaft and a base that is coupled to the shaft, the member comprising a cavity configured for disposal of at least one surgical instrument, the base including a body portion and a pair of spaced apart extensions that extend from the body portion, the extensions each including an inner surface having a protuberance extending outwardly therefrom such that the protuberances face one another, the protuberances each being configured for disposal in a detent in a spinal implant such that the member is rotatable relative to the spinal implant to selectively orient the at least one surgical instrument.

2. A surgical guide as recited in claim 1, wherein the shaft has a uniform dimension and the base has an increasing dimension.

3. A surgical guide as recited in claim 2, wherein the base has an elliptical configuration.

4. A surgical guide as recited in claim 1, wherein the extensions extend flexibly from the body portion.

5. A surgical guide as recited in claim 1, wherein the extensions are resiliently biased toward one another.

6. A surgical system comprising:
the surgical guide recited in claim 1; and
the implant, wherein the implant includes opposite top and bottom surfaces and a plurality of openings that each extend through the to and bottom surfaces, the implant comprising an edge that extends from the to surface to the bottom surface, the edge comprising the detents.

7. A surgical system comprising:
the surgical guide recited in claim 1; and
the at least one surgical instrument, wherein the at least one surgical instrument includes at least one of a plurality of alternate surgical instruments.

8. A surgical system comprising:
the surgical guide recited in claim 1; and
the at least one surgical instrument, wherein the at least one surgical instrument is selected from a drill, a tap and a driver.

9. A surgical system comprising:
the surgical guide recited in claim 1;
the implant; and
the at least one surgical instrument, wherein the member pivots about the implant to selectively orient the at least one surgical instrument relative to vertebral tissue.

10. A surgical guide as recited in claim 1, wherein the member rotates along a cephalad-caudal plane of a body.

11. A surgical guide as recited in claim 1, wherein the protuberances each have a hemi-spherical configuration.

12. A surgical guide as recited in claim 1, wherein a distance between the inner surfaces defines a maximum diameter of the cavity.

13. A surgical guide as recited in claim 1, wherein:
the shaft has a uniform dimension and the base has an increasing dimension; and
the member comprises a slot that extends from the base and into the shaft.

14. A surgical guide comprising:
a member including a uniform dimension shaft and a base having an increasing dimension; and
a wall that defines a cavity configured for disposal of at least one surgical instrument, the member including spaced apart first and second extensions, the first extension having a protuberance oriented in a first direction, the second extension having a protuberance oriented in a second, opposing direction,
wherein the extensions each flexibly extend from the base and the protuberances are configured for mating engagement with a spinal implant such that the member is rotatable relative to the spinal implant to selectively orient the at least one surgical instrument.

15. A surgical system comprising:
the surgical guide recited in claim 14; and
the implant, wherein the implant includes opposite top and bottom surfaces and a plurality of openings that each extend through the to and bottom surfaces, the implant comprising an edge that extends from the top surface to the bottom surface, the edge comprising a plurality of detents that are each configured for disposal of one of the protuberances.

16. A surgical system comprising:
a drill;
a guide comprising a member including a shaft and a base that is coupled to the shaft, the member comprising a cavity configured for disposal of the drill, the base including a body portion and a pair of spaced apart extensions that extend from the body portion, the extensions each including an inner surface having a protuberance extending outwardly therefrom such that the protrusions face one another;

a plate including opposite top and bottom surfaces and a plurality of openings that each extend through the to and bottom surfaces, the plate comprising an edge that extends from the to surface to the bottom surface, the edge comprising a plurality of detents that are each configured for disposal of one of the protuberances; and at least one screw configured for disposal in one of the openings, wherein the guide is configured for mating engagement with the plate such that the member is rotatable relative to the plate to selectively orient the drill.

17. A surgical system as recited in claim 16, wherein the member includes a distractor pin.

18. A surgical system as recited in claim 16, wherein the protuberances and the detents each have a hemi-spherical configuration.

19. A surgical system as recited in claim 16, wherein the protuberances are aligned with one another along a transverse axis such that the guide is pivotable relative to the plate about the transverse axis.

20. A surgical system as recited in claim 16, wherein the guide is rotatable and pivotable relative to the plate about a pivot point disposed in alignment with the openings.

* * * * *